United States Patent
Paul et al.

(10) Patent No.: US 10,286,348 B2
(45) Date of Patent: May 14, 2019

(54) FILTER AND METHOD FOR PRODUCING SAME

(71) Applicant: Lufthansa Technik AG, Hamburg (DE)

(72) Inventors: Manfred Paul, Nackenheim (DE); Patrick Luka, Moerfelden-Waldorf (DE); Rainer Pommersheim, Mainz (DE); Robert Sweredjuk, Dietmannsried-Reicholzried (DE)

(73) Assignee: LUFTHANSA TECHNIK AG, Hamburg (DE)

( * ) Notice: Subject to any disclaimer, the term of this patent is extended or adjusted under 35 U.S.C. 154(b) by 235 days.

(21) Appl. No.: 15/300,787

(22) PCT Filed: Mar. 27, 2015

(86) PCT No.: PCT/EP2015/056799
§ 371 (c)(1),
(2) Date: Sep. 30, 2016

(87) PCT Pub. No.: WO2015/150288
PCT Pub. Date: Oct. 8, 2015

(65) Prior Publication Data
US 2017/0021296 A1    Jan. 26, 2017

(30) Foreign Application Priority Data
Mar. 31, 2014   (DE) .................. 10 2014 206 081

(51) Int. Cl.
*B01D 53/02* (2006.01)
*B01D 46/00* (2006.01)
(Continued)

(52) U.S. Cl.
CPC .......... *B01D 46/0036* (2013.01); *A61L 9/014* (2013.01); *B01D 46/0001* (2013.01);
(Continued)

(58) Field of Classification Search
CPC ............. A61L 2209/14; A61L 2209/15; A61L 2209/22; A61L 9/014; B01D 2252/20473;
(Continued)

(56) References Cited

U.S. PATENT DOCUMENTS

| 5,194,414 A | 3/1993 | Kuma |
| 2003/0188850 A1 | 10/2003 | Liu et al. |

(Continued)

FOREIGN PATENT DOCUMENTS

| DE | 4200995 A1 | 8/1992 |
| DE | 202010009413 U1 | 9/2010 |

(Continued)

*Primary Examiner* — Christopher P Jones
(74) *Attorney, Agent, or Firm* — Leydig, Voit & Mayer, Ltd.

(57) ABSTRACT

A filter for binding constituents of a gas stream includes a supporting member and a filter layer applied to surfaces of the supporting member. The filter layer includes a component for the physisorption of constituents, a component for the chemisorption of constituents, and a component for dissolving oil constituents which comprises ionic liquids.

19 Claims, 2 Drawing Sheets

(51) Int. Cl.
*B01J 20/28* (2006.01)
*B01J 20/32* (2006.01)
*A61L 9/014* (2006.01)
*B01D 51/10* (2006.01)
*B01D 53/04* (2006.01)
*B01D 53/14* (2006.01)
*B01J 20/12* (2006.01)
*B01J 20/20* (2006.01)
*B01J 20/22* (2006.01)
*B01J 20/24* (2006.01)
*B64D 13/06* (2006.01)

(52) U.S. Cl.
CPC ............ *B01D 51/10* (2013.01); *B01D 53/02* (2013.01); *B01D 53/04* (2013.01); *B01D 53/1487* (2013.01); *B01D 53/1493* (2013.01); *B01J 20/12* (2013.01); *B01J 20/20* (2013.01); *B01J 20/22* (2013.01); *B01J 20/24* (2013.01); *B01J 20/2803* (2013.01); *B01J 20/28042* (2013.01); *B01J 20/324* (2013.01); *B01J 20/3204* (2013.01); *B01J 20/3236* (2013.01); *B01J 20/3238* (2013.01); *B01J 20/3274* (2013.01); *B01J 20/3287* (2013.01); *B01J 20/3295* (2013.01); *B64D 13/06* (2013.01); *A61L 2209/14* (2013.01); *A61L 2209/15* (2013.01); *A61L 2209/22* (2013.01); *B01D 2252/20473* (2013.01); *B01D 2252/30* (2013.01); *B01D 2253/102* (2013.01); *B01D 2253/11* (2013.01); *B01D 2253/20* (2013.01); *B01D 2253/25* (2013.01); *B01D 2253/342* (2013.01); *B01D 2257/702* (2013.01); *B01D 2258/06* (2013.01); *B01D 2259/4575* (2013.01); *B64D 2013/0618* (2013.01); *B64D 2013/0651* (2013.01); *B64D 2013/0688* (2013.01)

(58) Field of Classification Search
CPC ......... B01D 2252/30; B01D 2253/102; B01D 2253/11; B01D 2253/20; B01D 2253/25; B01D 2253/342; B01D 2257/702; B01D 2258/06; B01D 2259/4575; B01D 53/02; B01D 53/04; B01D 53/1487; B01D 53/1493
See application file for complete search history.

(56) References Cited

U.S. PATENT DOCUMENTS

| | | | |
|---|---|---|---|
| 2005/0053515 | A1 | 3/2005 | Yates et al. |
| 2009/0227195 | A1 | 9/2009 | Buelow et al. |
| 2010/0140175 | A1* | 6/2010 | Wyse ............... B01D 15/00 210/660 |
| 2010/0158775 | A1 | 6/2010 | Galligan et al. |
| 2013/0252526 | A1 | 9/2013 | Paul et al. |

FOREIGN PATENT DOCUMENTS

| | | |
|---|---|---|
| DE | 102012202563 A1 | 8/2013 |
| WO | WO 2013124168 A1 | 8/2013 |

* cited by examiner

FILTER AND METHOD FOR PRODUCING SAME

CROSS REFERENCE TO RELATED APPLICATIONS

This application is a U.S. National Stage Application under 35 U.S.C. § 371 of International Application No. PCT/EP2015/056799 filed on Mar. 27, 2015, and claims benefit to German Patent Application Nos. DE 10 2014 206 081.8 filed on Mar. 31, 2014. The International Application was published in German on Oct. 8, 2015 as WO 2015/150288 A1 under PCT Article 21(2).

FIELD

The invention relates to a filter for binding constituents of a gas stream, having a supporting member and a filter layer applied to the surfaces of the supporting member. The invention further relates to a method for producing such a filter, to the use of such a filter for filtering the respiratory air in modes of transport, in particular aircraft, and to an aircraft equipped with a filter according to the invention.

BACKGROUND

Many modes of transport, in particular aircraft and high-speed trains, are generally made pressure-tight and aerated artificially. Aircraft have a pressurized cabin in which, at cruising altitude, a cabin pressure above the outside air pressure is established.

The air is supplied to a pressurized cabin usually both by means of circulation and purification of cabin air as well as by mixing in fresh air introduced from outside. Since the outside pressure at cruising altitude is below cabin pressure, the fresh air to be introduced has to be compressed. As a rule for the fresh air feed, some of the airstream from the compressor of one or more aircraft engines (so-called bleed air) is diverted, cooled to a desired temperature level and mixed in with the cabin air.

The bleed air from jet engines can be contaminated with oil residues or oil mists, particularly if, for example, lubricating oil in the engine escapes in the region of the axle or the like and is entrained by the compressor airstream. The oils from jet engines can contain constituents or additives that are harmful to humans, such as, for example, tricresyl phosphate (TCP). Entrained oil residues can also lead to an unpleasant smell of oil in the aircraft cabin. Recirculated cabin air can likewise contain odorous substances or harmful substances.

In the prior art it is therefore already known to provide filter systems for the bleed air of engines and/or recirculated cabin air. Firstly, activated carbon filters, for example, are known from prior public use. These have only a relatively low absorption capacity and bind harmful substances by means of physisorption in a reversible manner, meaning that said substances can also be released again in the event of relatively high loading of an activated carbon filter.

It is also known to remove undesired constituents from cabin air by catalytic oxidation (for example US 2003/0188850 A1, US 2009/0227195 A1, US 2010/0158775 A1 and US 2005/0053515 A1). Such catalytic systems are very complex to install and operate since operating conditions have to be constantly observed that permit catalytic oxidation of the harmful substances, for example temperatures of more than 200° C. for thermal catalysis or introduction of UV radiation for photocatalysis. WO 2013/124168 A1 discloses filter granules for filtering respiratory air in commercial aircraft.

SUMMARY

In an embodiment, the present invention provides a filter for binding constituents of a gas stream. The filter includes a supporting member and a filter layer applied to surfaces of the supporting member. The filter layer includes a component for the physisorption of constituents, a component for the chemisorption of constituents, and a component for dissolving oil constituents which comprises ionic liquids.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
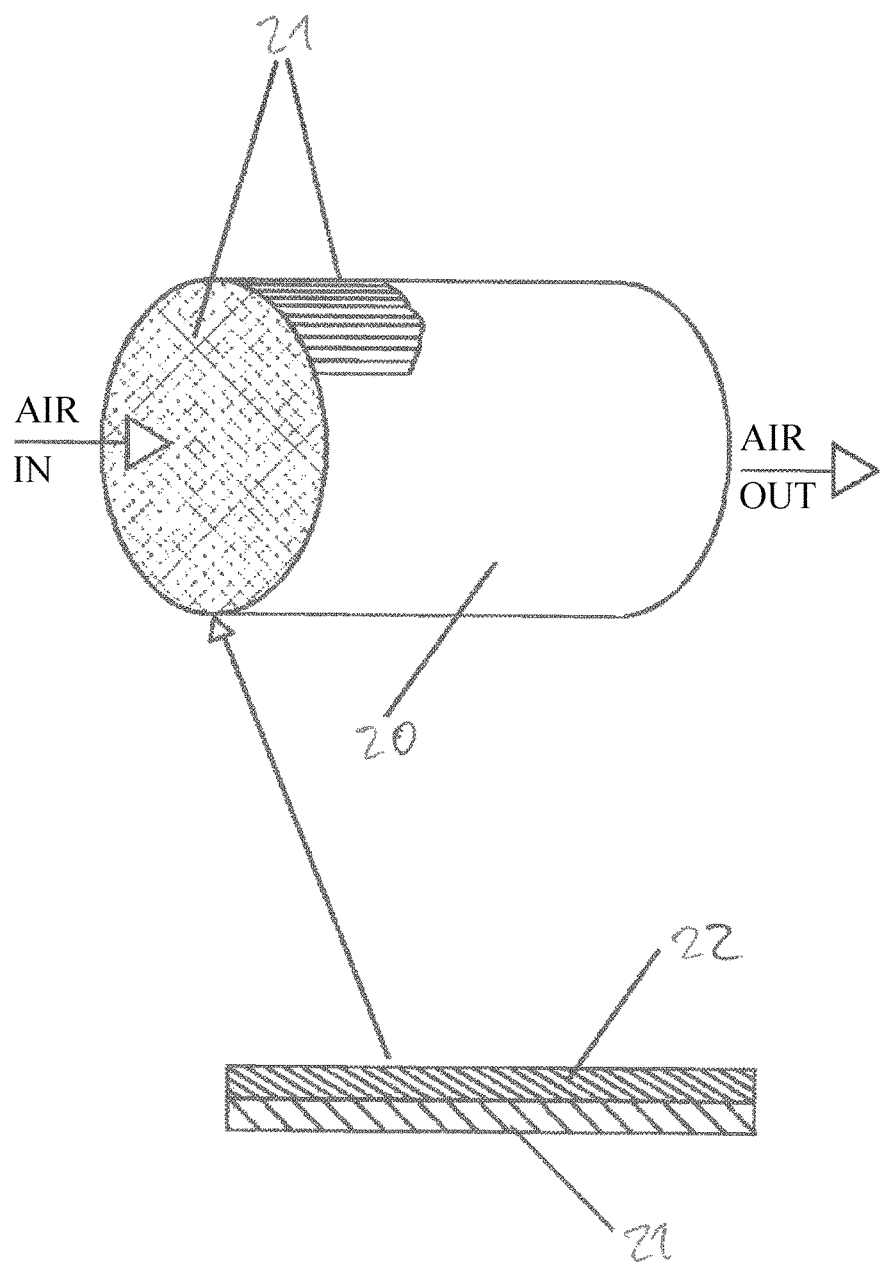
FIG. 1 depicts, diagrammatically, a filter according to an embodiment of the invention.

An easy-to-handle and effective option for removing harmful substances such as, for example, oil residues from a gas stream, in particular the bleed air or cabin air of aircraft, that can be integrated into existing systems easily and without major problems is described herein.

A filter layer having the following components is described herein:

a) a component for the physisorption of constituents,
b) a component for the chemisorption of constituents,
c) a component for dissolving oil constituents which comprises ionic liquids.

A method is described herein for producing a filter, the use of such a filter for filtering the respiratory air in modes of transport, in particular aircraft; as well as aircraft equipped with filters according to the invention.

The term supporting member, as used herein, can refer to a substrate over or through which a gas stream can flow and the surfaces of which can at least in part carry the filter layer described in more detail below. Suitable supporting members are supporting members for exhaust gas catalysts known for example from automobile technology. Such supporting members have a large surface based on their volume combined with a low throughflow resistance, which makes it possible for large amounts of gas to flow through.

A filter layer can be applied to surfaces of the supporting member. It interacts with passing gas and exerts the desired filter effect. The type and thickness of the filter layer are dimensioned such that the required through-flowability of the filter is still ensured.

As described herein, three components can be present in the filter layer. The term component in this context can be understood in functional terms and can refer to parts or constituents of a layer which can perform the described function.

A first component serves for the physisorption of constituents of the gas stream. During the physisorption, an absorbed molecule is bound to the surface of the component (of the physisorbing substrate) by generally comparatively weak physical forces (binding energies often in the range 4-40 kJ/mol). The physisorption generally does not lead to a chemical change of the absorbed substances and is usually reversible.

A further component serves for the chemisorption of constituents of the gas stream. During the chemisorption, the absorbate (the bound constituent of the gas stream) and/or the absorbent (the component which forms the substrate for the chemisorption) is chemically changed. Binding energies can be for example in the region around 800 kJ/mol. The chemisorption is generally irreversible, i.e. the chemisorbed constituents are bound permanently.

As described herein, a third component serves for dissolving oil constituents. The term oil constituents can refer to constituents entrained in the gas stream, for example of the lubricating oil of a jet engine, generally such oil constituents are in the form of an aerosol finely distributed in the gas stream. The stated component comprises a solvent which can transfer oil constituents to solution and thereby remove them from the gas stream. The vapor pressure of the solvent and the associated solution of the oil constituents is so low according to the invention that, under the operating conditions of the corresponding filter, solvent and/or solution are not introduced into the gas stream to a noteworthy degree. The solvents used are the ionic liquids described in more detail below.

A filter according to an embodiment of the invention combines three components and thus also three functions. The component for the physisorption can be selected for example according to the invention from the group consisting of activated carbon, siliceous earths, zeolites and bentonite and brings about a rapid and effective depletion of constituents of the gas stream accessible to the physisorption, such as, for example, air pollutants, odors or the like.

The chemisorbing component permits a permanent and thus irreversible binding of corresponding undesired constituents of the gas stream. It is also possible in the context of the invention that constituents of the gas stream are firstly physisorbed and thereby localized in the region of the filter and then a chemisorption and thus permanent binding takes place.

The component for dissolving oil constituents permits a permanent and certain removal of corresponding oil aerosols from a gas stream, thereby effectively preventing the introduction of undesired oil odors and harmful substances from lubricating oil into the cabin air of the aircraft. The removal of these oil constituents by dissolving in a solvent binds the oil constituents permanently and moreover has a high absorption capacity.

A filter according to an embodiment of the invention thus permits a certain and rapid, but also permanent and irreversible removal of typical constituents of odors and harmful substances from a gas stream, in particular the respiratory air of an aircraft cabin.

As described herein, the specified components can be constituents of a filter layer on a supporting member. The invention has recognized that the configuration of the filter as supporting member with filter layer applied thereto permits the creation of a filter which, on the one hand, permits a high gas throughput with good filter effect and, on the other hand, has a low flow resistance, meaning that it can be integrated directly and in particular without additional measures into existing systems, for example systems for supplying an aircraft cabin with respiratory air. In particular, it is generally not required according to the invention to provide measures such as, for example, pressure increase or increased pumping rate during the supply of respiratory air in order to compensate for a large flow resistance of a filter.

According to an embodiment of the invention, the supporting member is preferably selected from the group consisting of ceramic supporting members and metal supporting members. Supporting members made of plastic can likewise be used. In particular, the supporting members used may be like those found as catalyst supports in the exhaust gas technology of automobiles. Supporting members made of metal can for example have cavities or cells in the form of honeycombs, suitable supporting members are described for example in WO 2010/108755 A1. Suitable supporting members are commercially available for example under the name METALIT® from Emitec Gesellschaft für Emissionstechnologie GmbH.

According to an embodiment of the invention, the cell densities of the supporting members used can preferably be in the range 50 to 1600 cpsi (cells per square inch), further preference being given to ranges from 100 to 1000 cpsi and from 150 to 500 cpsi. The thickness of the cell walls is preferably in the range 10-100 μm, further preferably 10-50 μm. The shape of the cells in cross section (sectional plane perpendicular to the direction of flow) can be, for example, sinusoidal, quadratic, triangular or hexagonal.

The supporting member according to an embodiment of the invention can have a cladding, which can for example have a wall thickness of 0.5-5 mm, further preferably 1-2 mm. The cladding serves to stabilize the supporting member. Alternatively, it is possible to dispense with a cladding and to insert the supporting member in an essentially form-fitting manner into a flow channel, the walls of which stabilize the supporting member.

The length of a supporting member in the flow direction can be according to an embodiment of the invention for example 10-1000 mm, preferably 10-100 mm. The pressure loss brought about by the filter according to the invention is preferably 10 mbar or less, further preferably 5 mbar or less.

The component for the physisorption can be selected from the group consisting of activated carbon, bentonite, siliceous earths, and zeolites.

As described herein, the component for the chemisorption can comprise suitable amino acids or amino acid sequences, in particular peptides or proteins. Peptides are generally shorter-chain than proteins, there being a fluid transition between the two term categories. Such peptides or proteins can bind harmful substances by chemisorption, which are so-called protein-reactive substances, i.e. compounds which react with proteins or protein derivatives of the component for the chemisorption and enter into a chemical bond. These include typical air pollutants such as aldehydes (in particular formaldehyde) and many volatile organic compounds (VOCs). Suitable amino acid sequences can be produced for example by hydrolysis of proteins such as, for example, scleroproteins, it also being possible to use, for example, keratin-containing fibers such as, for example, sheeps wool fibers.

As described herein, the component for dissolving oil constituents can comprise ionic liquids. Ionic liquids are salts which are generally liquid at the operating temperatures of the filter. Typically, ionic liquids are liquid at temperatures below 100° C., preferably also at room temperature. Ionic liquids have a very low, barely measurable vapor pressure and have good dissolving properties for oil constituents. In ionic liquids according to the invention, the cations are preferably selected from the group consisting of optionally alkylated imidazolium, pyridinium, pyrrolidinium, guanidinium, uronium, thiouronium, piperidinium, morpholinium, ammonium and phosphonium ions and the anions selected from the group consisting of tetrafluoroborates, trifluoroacetates, triflates, hexafluorophosphates, phosphinates, tosylates, imides, amides, sulfates and halides.

In an advantageous embodiment of the invention, the filter layer has a matrix. The term matrix refers to a substance which serves as structure former and carries the described components. Constituents of the matrix can comprise components for the physisorption and/or chemisorption. The matrix can also comprise binders, for example binders selected from the group consisting of mannurone, gulurone, alginate and pectin salts. These binders can be provided for example as alkali metal salts firstly in aqueous solution and be mixed with other components. As a result of exchanging the alkali metal ions for, for example, alkaline earth metal ions (in particular $Ca^{2+}$ ions), it is possible to make insoluble salts from the soluble salts and these thus precipitate out or gel and in so doing localize or fix corresponding filter layers. According to the invention, it is likewise possible to bring about the gelation by means of suitable organic cations, for example oligomeric or polymeric cations such as PEI (polyethylenimines), PDMDAAC (poly(dimethyldiallylammonium chloride) or PLL (poly-L-lysine). Surprisingly, the invention has recognized that cations of the ionic liquid used can also be used for the gelation and/or contribute thereto.

One such matrix with the specified binders can also incorporate or encapsulate ionic liquids. The encapsulation of oils in a matrix made of an alkali metal alginate is described for example in U.S. Pat. No. 4,389,419. This specification forms part of the subject matter of the present disclosure by reference.

A method for producing a filter is described herein that is characterized by the following steps:
 a) provision of a supporting member,
 b) coating of the surfaces of the supporting member with a filter layer.

Preferably, the surfaces of the supporting member are coated with a solution of constituents of the filter layer. This can be effected by immersing the supporting member into such a solution or spraying with the solution. After the coating, a fixing can preferably be effected. This takes place preferably by solidifying a binder of the filter layer. The solidification can take place through the action of temperature or preferably by means of chemical reactions. In particular, the reaction can be triggered by applying a further component.

If the binders are selected, for example, from the group consisting of mannurone, gulurone, alginate and pectin salts, they can be provided for example as alkali metal salts firstly in aqueous solution and be mixed with further components. This aqueous solution is applied to the surfaces of the supporting member, for example by immersion. By replacing the alkali metal ions with, for example, alkaline earth metal ions, it is possible to make insoluble salts from the soluble salts, and these thus precipitate out or gel and in so doing localize or fix corresponding filter layers. This can be effected by immersion in or spraying on of a solution of alkaline earth metal ions.

The use of a filter for filtering the respiratory air in modes of transport, in particular aircraft, is described herein. According to an embodiment of the invention, the filtering of bleed air can take place before it is passed for the first time to the air conditioning system of the cabin in order to remove oil residues or other harmful substances originating from the compressor tract of the engine. Alternatively or additionally, recirculated cabin air can be filtered in order to also remove other harmful substances in the air, odors or the like.

An aircraft which contains at least one filter is described herein. The filters can be used for the purification of bleed air or recirculated cabin air and be arranged at one or more of the following installation sites:
 between bleed air valve and cooling unit,
 between cooling unit and mixing unit,
 between mixing unit and exit of the supply pipes to cabin and/or cockpit.

Preferably, the arrangement is within the pressurized cabin before the exit of the supply pipes to the cabin and/or cockpit.

FIG. 1 shows diagrammatically a filter 20 according to an embodiment of the invention. In its inside there is a supporting member 21 with a structure in the form of honeycombs. As can be seen in the lower detail section of FIG. 1, a filter layer 22 is applied to the surface of the supporting member 21. In this working example, the filter has a cell density of 200 cpsi. The cell walls consist of a 40 µm-thick metal alloy film made of the material DIN 1.4767 (aluminum-containing ferritic chromium steel alloyed with yttrium and hafnium). The cladding of the filter has a thickness of 1.5 mm, the material of the cladding is a metal alloy DIN 1.4509 (stainless ferritic chromium steel). The length of the cladding is 84.5 mm, the cladding overhang relative to the filter matrix is 5 mm at each longitudinal end.

The production of a filter according to the invention is described below.

Example 1

The following constituents are dissolved or dispersed in 900 ml of water:
 80-100, preferably 90 g bentonite
 30-60, preferably 45 g activated carbon
 20-50, preferably 35 g ethyl methylimidazolium ethylsulfate
 2-8, preferably 5 g N-(L-α-aspartyl)-L-phenylalanine methyl ester
 4-8, preferably 6 g sodium alginate.

The solution or dispersion prepared in this way is applied to the supporting member 21, the supporting member preferably being immersed into these solutions. The supporting member pretreated in this way is then immersed into a 2% strength aqueous calcium chloride solution. As a result of adding calcium (or other suitable polyvalent metal cations), insoluble alginate salts are formed which cause the filter layer to gel and to solidify. Drying is then carried out in a stream of air. In the next step, ionic liquid is additionally applied to the fixed filter layer. For this purpose, the supporting member is immersed into 1-ethyl-2-methylimidazolium ethylsulfate, or this ionic liquid is sprayed on and dried in a stream of air.

Example 2

The solution or mixture described in example 1 is prepared as in that example and applied to the surfaces of the supporting member. The fixing of this filter layer, however, takes place in the second step directly by immersing the supporting member into 1-ethyl-2-methylimidazolium ethylsulfate and subsequent drying in a stream of air. In this variant of the invention, the fixing or gelation of the filter layer is thus carried out in a single step and the ionic liquid is applied.

Figure 2:
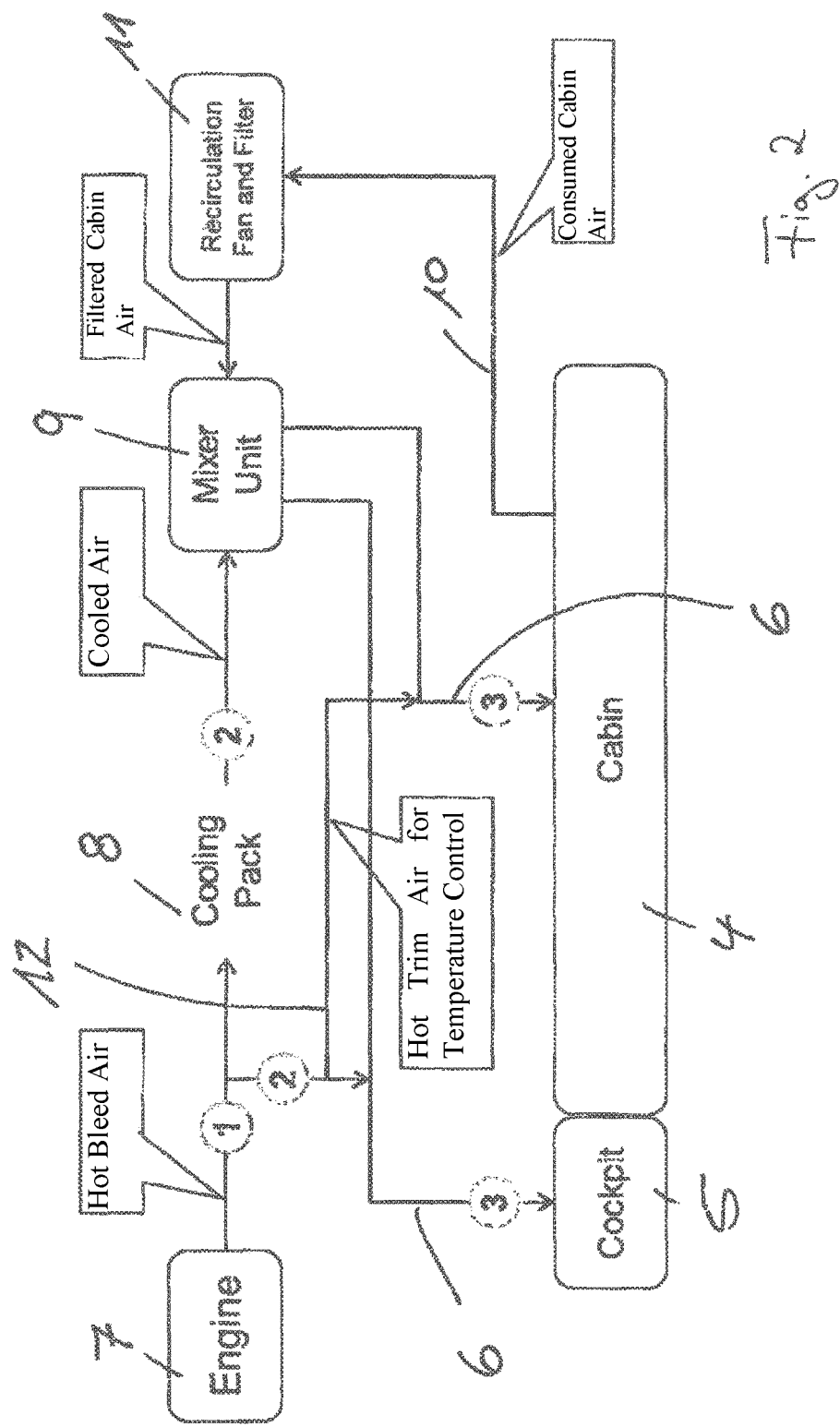
FIG. 2 depicts, diagrammatically, an air conditioning system of a commercial aircraft according to an embodiment of the invention.

FIG. 2 shows diagrammatically the air conditioning system of a commercial aircraft according to an embodiment of the invention. A cabin 4 and a cockpit 5 of an aircraft are fed with air from supply pipes 6. This air is a mixture of temperature-adjusted fresh air and filtered, recirculated cabin air.

The fresh air is provided by diverting so-called bleed air from the compressor of one or more engines 7. The majority of the bleed air heated on account of the compression (temperature typically 215-260° C.) is passed to a cooling unit 8 and cooled to the desired temperature. The cooled stream of air is fed to a mixing unit 9.

Spent cabin air is removed by suction from the cabin using a line 10 and purified in a device 11 for the recirculation and filtering of cabin air. This device 11 works according to the prior art. In the mixing unit 9, purified, recirculated cabin air and cooled fresh air is mixed in a pregiven ratio and fed via the supply pipes 6 to the cockpit and the cabin. To regulate the temperature in the cabin, some of the hot, still not cooled bleed air can be diverted via the line 12 and mixed with the stream of air passed from the mixing unit 9 to cockpit 5 and cabin 4.

Filters according to embodiments of the invention can be incorporated into such an air conditioning system at different positions, which are labeled in the figure with the reference numerals 1, 2 and 3.

In the case of installation site 1, the still-hot bleed air is filtered directly after its removal from the engine 7. This installation site has the advantage that any oil residues present in the bleed air are filtered directly after exiting from the engine and are unable to enter the air conditioning system. A disadvantage of this position is particularly the hindered operating conditions as a result of high temperature, high flow rate and high pressure, which hinder the efficient operation of a filter according to the invention.

In the case of possible installation site 2, on the one hand, the already cooled bleed air and, on the other hand, the hot part of the bleed air diverted for the purposes of temperature regulation is purified by means of at least one filter according to the invention in each case. What is problematic here is in particular the fact that two streams of air with in particular very different temperatures have to be filtered.

It is preferred to provide filters according to the invention at installation site 3 and to filter the already temperature-adjusted air directly prior to its introduction into cockpit 5 or cabin 4.

This installation site 3 has various advantages. At this installation site, relatively cool air with a temperature that varies little passes through the filters. The temperature of the airstream at installation site 3 is in every case below 100° C. and therefore permits a relatively simple construction of the filter as a consequence of it not necessarily having to be thermally resistant. The cross section of the supply pipes 6 is generally large (typical diameter for example 150-164 mm), this permits a correspondingly large and therefore effective cross section of the filter, through which, moreover, less compressed air flows at a low flow rate. The installation site 3, moreover, is readily accessible for maintenance purposes since it is located inside the pressurized cabin, for example access is possible via corresponding openings in the front cargo area of an aircraft. The number of required installation sites 3 can vary depending on the type of aircraft. For a commercial passenger aircraft of the A320 family, for example, five filters are required; and for a Boeing 737 three filters are required.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A filter for binding constituents of a gas stream, the filter comprising:
    a supporting member; and
    a filter layer applied to the surfaces of the supporting member,
    wherein the filter layer includes:
        a) a component for the physisorption of constituents,
        b) a component for the chemisorption of constituents, and
        c) a component for dissolving oil constituents which comprises ionic liquids,
    wherein the supporting member has a cell density of from 50 to 1600 cpsi.

2. The filter as claimed in claim 1, wherein the supporting member is at least one of a ceramic supporting member or a metal supporting member.

3. The filter as claimed in claim 1, wherein, under application conditions, the filter has a pressure drop of 10 mbar or less.

4. The filter as claimed in claim 1, wherein the component for the physisorption includes at least one of activated carbon, bentonite, siliceous earths, or zeolites.

5. The filter as claimed in claim 1, wherein the component for the chemisorption comprises at least one of peptides or proteins.

6. The filter as claimed in claim 1, wherein the component for the chemisorption comprises keratin-containing fibers.

7. The filter as claimed in claim 1, wherein the ionic liquids comprise cations selected from the group consisting of: optionally alkylated imidazolium, pyridinium, pyrrolidinium, guanidinium, uronium, thiouronium, piperidinium, morpholinium, ammonium and phosphonium ions and anions selected from the group consisting of tetrafluoroborates, trifluoroacetates, triflates, hexafluorophosphates, phosphinates, tosylates, imides, amides, sulfates and halides.

8. The filter as claimed in claim 1, wherein the filter layer has a matrix, wherein constituents of the matrix comprise components for the physiosorption and/or components for the chemisorption.

9. The filter as claimed in claim 8, wherein the matrix comprises binders.

10. The filter as claimed in claim 9, wherein the binders include at least one of mannurone, gulurone, alginate, or pectin salts.

11. The filter as claimed in claim 8, wherein the matrix incorporates ionic liquids.

12. A method for producing a filter, the method comprising:
   a) provision of a supporting member,
   b) coating of the surfaces of the supporting member with a filter layer, wherein the filter layer includes:
      a component for the physisorption of constituents,
      a component for the chemisorption of constituents, and
      a component for dissolving oil constituents which comprises ionic liquids,
      wherein the supporting member has a cell density of from 50 to 1600 cpsi.

13. The method as claimed in claim 12, wherein the surfaces of the supporting member are coated with a solution of constituents of the filter layer.

14. The method as claimed in claim 13, wherein, after the coating with a solution of constituents of the filter layer, a fixing takes place.

15. The method as claimed in claim 14, wherein the fixing takes place by solidifying a binder of the filter layer.

16. The method as claimed in claim 15, wherein the solidification of the binder takes place through a reaction by means of applying a further component.

17. An aircraft, comprising:
   a filter for the filtering of the respiratory air, the filter comprising:
      a supporting member; and
      a filter layer applied to the surfaces of the supporting member,
   wherein the filter layer includes:
      a) a component for the physisorption of constituents,
      b) a component for the chemisorption of constituents, and
      c) a component for dissolving oil constituents which comprises ionic liquids.

18. The aircraft as claimed in claim 17, wherein the filter is arranged at one of the following installation sites:
   between a bleed air valve and a cooling unit,
   between a cooling unit and a mixing unit,
   between a mixing unit and an exit of supply pipes to a cabin and/or a cockpit.

19. The aircraft as claimed in claim 18, wherein the filter is arranged within a pressurized cabin before the exit of the supply pipes to the cabin and/or the cockpit.

* * * * *